(12) United States Patent
Aiken et al.

(10) Patent No.: US 8,703,978 B2
(45) Date of Patent: *Apr. 22, 2014

(54) PHOTOCHROMIC DICHROIC NAPHTHO-PYRANS AND OPTICAL ARTICLES CONTAINING THEM

(75) Inventors: Stuart Aiken, North Yorkshire (GB); Christopher David Gabbutt, Lancashire (GB); Bernard Mark Heron, East Yorkshire (GB); Christopher Stephen Kershaw, Bristol (GB); Nicola Jane Smith, North Yorkshire (GB); Jean-Paul Cano, Charenton-le-Pont (FR)

(73) Assignee: Essilor International (Compagnie Generale d'Optique), Charenton-le-Pont (FR)

( * ) Notice: Subject to any disclaimer, the term of this patent is extended or adjusted under 35 U.S.C. 154(b) by 364 days.

This patent is subject to a terminal disclaimer.

(21) Appl. No.: 12/919,626

(22) PCT Filed: Mar. 2, 2009

(86) PCT No.: PCT/EP2009/052452
§ 371 (c)(1),
(2), (4) Date: Dec. 6, 2010

(87) PCT Pub. No.: WO2009/109546
PCT Pub. Date: Sep. 11, 2009

(65) Prior Publication Data
US 2011/0122475 A1    May 26, 2011

(30) Foreign Application Priority Data

Mar. 5, 2008  (EP) .................................... 08300136

(51) Int. Cl.
*C07D 311/92*  (2006.01)

(52) U.S. Cl.
USPC ........................................................ 549/389

(58) Field of Classification Search
USPC ........................................................ 549/389
See application file for complete search history.

(56) References Cited

U.S. PATENT DOCUMENTS

| 5,650,098 | A  | * | 7/1997 | Kumar et al. .................. 252/586 |
| 7,229,989 | B2 | * | 6/2007 | Mann et al. .................. 514/228.5 |
| 2005/0096467 | A1 | * | 5/2005 | Mann et al. .................... 540/596 |

FOREIGN PATENT DOCUMENTS

WO    WO 03/080595    10/2003

OTHER PUBLICATIONS

Dorwald F. A. Side Reactions in Organic Synthesis, 2005, Wiley: Vch, Weinheim p. IX of Preface p. 1-15.*

* cited by examiner

*Primary Examiner* — Nizal Chandrakumar
(74) *Attorney, Agent, or Firm* — Occhiuti & Rohlicek LLP

(57) ABSTRACT

A naphthopyran compound represented by the formulae (I) to (II) wherein: —mi, Hi2, p, q are each an integer comprised from O to 4 or 5 inclusive; —Ri, R2 and R4, represent a group selected from halogen, H, —Ra, aryl, —OH, —ORa, —SH, —SRa, —NH2, —NR8RaI, —NRbRc, —NRaI-CORa, —NRaiCO(aryl), —NRai aryl, —N-aryfe, —N(aryl)CO (aryl), —CO—R3, —CO2R3I, —OC(O)—Rd, and —X— (Re)—Y, and linear or branched (Ci-Ci8) perfluoroalkyl group, wherein R3, Rai, Rb, Rc, X, Y, Re, Rd are as defined into the description; —Zi re resent a group selected from: (formules).

3 Claims, 1 Drawing Sheet

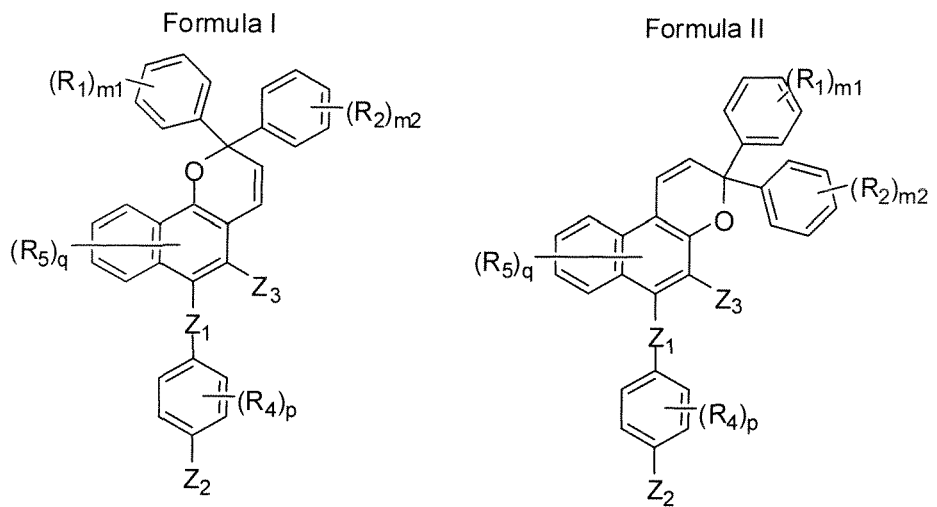
Formula I
Formula II
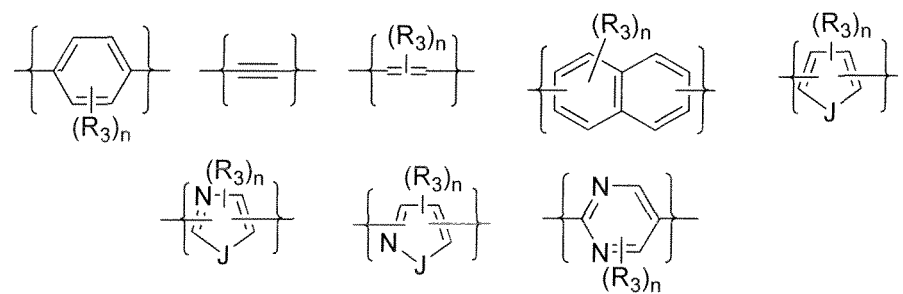
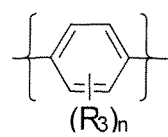

PHOTOCHROMIC DICHROIC NAPHTHO-PYRANS AND OPTICAL ARTICLES CONTAINING THEM

CROSS-REFERENCE TO RELATED APPLICATIONS

This application is the National Stage of International Application No. PCT/EP2009/052452, filed on Mar. 2, 2009, which claims the priority of European Application No. 08300136.2 filed on Mar. 5, 2008, the contents of which are incorporated herein by reference in their entirety.

The present invention relates to a group of novel dyes that are photochromic and to the use thereof in optical articles, especially in optical lenses such as ophthalmic lenses.

Photochromism is a well known physical phenomenon which is observed with certain classes of chemical compounds. A detailed discussion of this phenomenon can be found in "Photochromism: Molecules and Systems", Studies in Organic Chemistry 40, edited by H. Dürr and H. Bouas-Laurent, Elsevier, 1990 and a recent review specific to 2H-naphtho[1,2-b]pyrans and 3H-naphtho[2,1-b]pyrans in Functional Dyes, edited by S—H. Kim, Elsevier, 2006, pp 85-136.

Passive photochromic devices, i.e. devices containing photochromic dyes whose absorbance depends only from the presence or absence of UV light, typically exhibit rather quick activation (coloration) but it generally takes several minutes or even tens of minutes to revert from the coloured to the bleached state. This slow fading is a severe drawback for the user of photochromic glasses who has to take them off to have clear vision when leaving the sunlight and entering dimmer light conditions.

The Applicants have undertaken extensive research aiming to provide new photochromic dyes exhibiting not only good photochromic properties, such as high absorption in the coloured state, fast colouring and fading rates, but which also may be capable of dichroism and linear light polarization when in a spatially ordered condition, for example when incorporated into liquid crystals or oriented polymer host materials.

The Applicants now have synthesized a group of new photochromic 2H-naphtho[1,2-b]pyrans and 3H-naphtho[2,1-b] pyrans having a mesogenic substituted group at C-6 of the naphthopyran nucleus. These new compounds have dichroic properties.

Incorporation of the mesogenic group, such at least two functional group selected from aryl, ethynyl, ethenyl, and heteroaryl, significantly improves the dichroic properties of the photochromic dyes in the activated state, and also influences the state of the dyes at room temperature. The new dyes when incorporated into anisotropic host materials such as liquid crystals or oriented polymers will strongly align with the host material molecules and exhibit strong dichroism, i.e. light polarizing, in the coloured state.

The Applicants further have observed that the new photochromic dyes of the present invention exhibit a fast fading rate, especially when dissolved in a fluid, mesomorphous or gel host medium, They are able to revert from the coloured to the bleached state in a short time, typically in less than five minutes, which constitutes an important advantage over most of the prior art photochromic dyes.

Accordingly, the present invention provides a group of new naphthopyran compounds represented by the formulae (I) to (II)

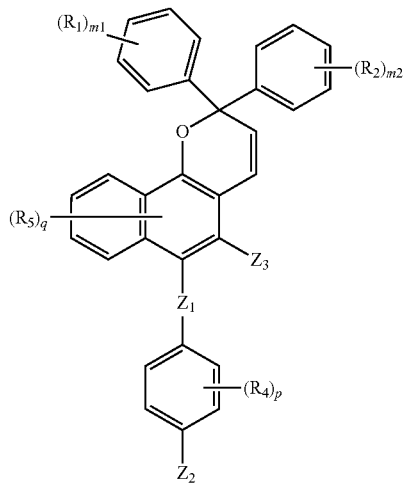

Formula I

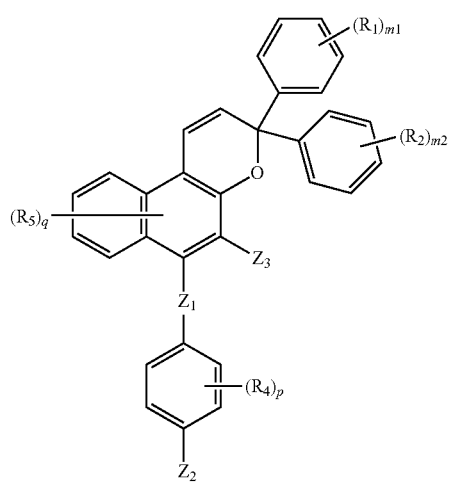

Formula II wherein:
$m_1$ is an integer comprised from 0 to 5 inclusive;
$m_2$ is an integer comprised from 0 to 5 inclusive;
p is an integer comprised from 0 to 4 inclusive;
q is an integer comprised from 0 to 4 inclusive
$R_1$, $R_2$ and $R_4$, identical or different, independently from each other, represent a group selected from halogen, H, —$R_a$, aryl, —OH, —$OR_a$, —SH, —$SR_a$, —$NH_2$, —$NR_aR_{a1}$, —$NR_bR_c$, $NR_{a1}COR_a$, —$NR_{a1}CO(aryl)$, $NR_{a1}aryl$, —N-aryl$_2$, —N(aryl)CO(aryl), —CO—$R_a$, —$CO_2R_{a1}$, —OC(O)—$R_a$, and —X—($R_e$)—Y, and linear or branched ($C_1$-$C_{18}$) perfluoroalkyl group, wherein:
$R_a$ represents a linear or branched ($C_1$-$C_{18}$) alkyl group or
$R_{a1}$ represents a group selected from hydrogen, linear or branched ($C_1$-$C_{18}$) alkyl group, and linear or branched ($C_1$-$C_{18}$) perfluoroalkyl group;
$R_b$ and $R_c$,
together and in combination with the nitrogen atom, represent a saturated 5 to 7 membered heterocyclic group which comprises optionally one additional heteroatom selected from O, N and S, and which may be optionally substituted by one or two group(s), identical or different, selected from halogen, —$R_a$, —OH, —$OR_a$, —$NH_2$, and —$NR_aR_{a1}$, wherein $R_a$ and $R_{a1}$ are as defined hereinbefore, or together and in combination with the nitrogen atom and the adjacent phenyl group form a heterocyclic group of formula (A), (B), (C) or (D) wherein t is an integer comprised from 0 to 2 inclusive, and $R_a$ and $R_{a1}$ are as defined hereinbefore:

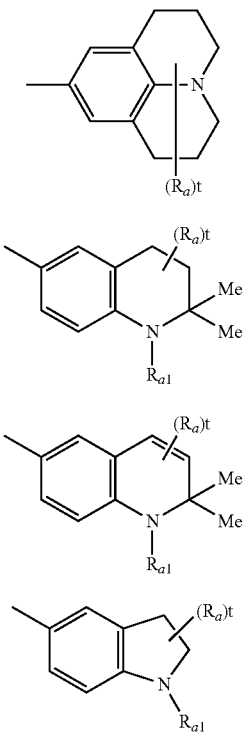

X represents a group selected from oxygen atom, —N($R_{a1}$)—, sulphur atom, —S(O)— and —S($O_2$)— wherein $R_{a1}$ is as defined hereinbefore;

Y represents a group selected from –O$R_{a1}$, N$R_{a1}R_{a2}$, and —S$R_{a1}$ wherein $R_{a1}$ is as defined hereinbefore and $R_{a2}$ represent a group selected from hydrogen and linear or branched ($C_1$-$C_{18}$) alkyl group;

$R_e$ represents a linear or branched ($C_1$-$C_{18}$) alkylene group, which may be optionally substituted by a group selected from halogen, hydroxyl, linear or branched ($C_1$-$C_6$) alkoxy, and amino;

$R_d$ represents a group selected from linear or branched ($C_1$-$C_{18}$) alkyl group, linear or branched ($C_1$-$C_{18}$) perfluoroalkyl group, —($R_e$)—Y, and aryl group which is optionally substituted by 1 to 4 groups selected from halogen, —$R_a$, —OH, —O$R_a$, —SH, —S$R_a$, —$NH_2$, —$NR_aR_{a1}$, —$NR_bR_c$, —CO—$R_a$, —$CO_2R_{a1}$ wherein $R_a$, $R_{a1}$, $R_b$, $R_c$, $R_d$, $R_e$ and Y are as defined hereinbefore;

$Z_1$ represent a group selected from:

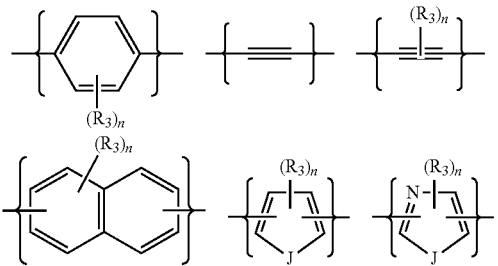

wherein:
$R_3$ represents a group selected from halogen, —$R_a$, —OH, —O$R_a$, —SH, —S$R_a$, —$NH_2$, and —$NR_aR_{a1}$, each or $R_3$ being identical or different;

J is selected from O, S, N$Ra_1$, wherein $R_{a1}$ is as defined hereinbefore;

n is an integer comprised from 0 to 6 inclusive;

$R_5$ represents a group selected from:
halogen, —$R_a$, —OH, —O$R_a$, —SH, —S$R_a$, —$NH_2$, —$NR_aR_{a1}$, —CO—$R_a$, —O—C(O)—$R_a$, and —$CO_2R_{a1}$ wherein $R_a$ and $R_{a1}$ are as defined hereinbefore, or when q is equal to 2 and then two $R_5$ substituents are located onto two adjacent carbon atoms selected from C-7, C-8, C-9 and C-10 of the naphtho[2,1-b]pyran or naphtho[1,2-b]pyran group, they may further represent together a group —O—($CH_2$)$_{q1}$—O— wherein q1 represents an integer comprised from 1 to 3 inclusive.

$Z_2$ represents a group selected from H, halogen, —$R_a$, —OH, —O$R_a$, —SH, —S$R_a$, —$NH_2$, —$NR_aR_{a1}$, —CO—$R_a$, —$CO_2R_{a1}$, and —O—Z—$R_6$, wherein $R_a$ and $R_{a1}$ are as defined hereinbefore;

$R_6$ represents a group selected from:
—$R_a$ which may be optionally substituted by a group selected from halogen, —OH, —O$R_a$, —SH, —S$R_a$, —$NH_2$, —$NR_aR_{a1}$, —CO—$R_a$, and —$CO_2R_{a1}$, wherein $R_a$ and $R_{a1}$ are as defined hereinbefore;

cycloalkyl, heterocycloalkyl, aryl, heteroaryl, which may be optionally substituted by 1 to 4 groups selected from halogen, —OH, —O$R_a$, —SH, —S$R_a$, —$NH_2$, —$NR_aR_{a1}$, —CO—$R_a$, —O—C(O)—$R_a$ and —$CO_2R_{a1}$, Z represents a group selected from CO, CS, SO, $SO_2$, $CO_2$, C(O)S, $CS_2$, C(O)NH, C(O)N$R_a$, C(S)NH, C(S)N$R_a$ and C=N$R_a$, wherein $R_a$ is as defined hereinbefore $Z_3$ represents a group selected from hydrogen, —$CO_2R_{a1}$, CHO, —$CH_2$OH, —$CH_2OR_{a1}$, —$CR_aR_{a1}$OH, —$R_{a1}$, and linear or branched ($C_2$-$C_{18}$) alkenyl;

with the provision that for compounds of formula (II) when $Z_1$ represents a group

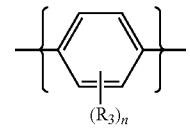

then $Z_3$ is not a hydrogen.

It is understood that in the present invention:
cycloalkyl means a 3 to 12 membered carbocycle, which may be monocyclic or bicyclic;
heterocycloalkyl means a cycloalkyl as defined hereinbefore comprising from 1 to 2 heteroatoms selected from oxygen, nitrogen and sulphur;
aryl means a phenyl group or a naphthyl group;
heteroaryl means a 3 to 10 membered monocycle or bicycle comprising from 1 to 3 heteroatom(s) selected from oxygen, nitrogen and sulphur;

halogen means an atom selected from bromine, chloride, iodine, and fluorine;

linear or branched ($C_1$-$C_{18}$) perfluoroalkyl group means a linear or branched ($C_1$-$C_{18}$) alkyl group wherein substantially all hydrogen atoms are substituted by fluorine atoms.

In one embodiment, preferred naphthopyrans according to the present invention are compounds of formula (I) and (II), and more preferably compounds of formula (I) and (II) wherein $Z_1$ represent a group selected from:

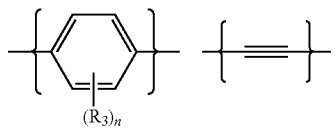

In another embodiment, preferred naphthopyrans according to the present invention are compounds of formula (I)-(IV) selected from the group consisting of:

Methyl 6-(4'-dodecyloxybiphenyl-4-yl)-2-phenyl-2-(4-pyrrolidinophenyl)-2H-naphtho[1,2-b]pyran-5-carboxylate Methyl 2-(4-diethylaminophenyl)-2-phenyl-6-(4'-pentylbiphenyl-4-yl)-2H-naphtho[1,2-b]pyran-5-carboxylate Methyl 6-(4'-pentylbiphenyl-4-yl)-2-phenyl-2-(4-pyrrolidinophenyl)-2H-naphtho[1,2-b]pyran-5-carboxylate 6-[(4-Dibutylaminophenyl)ethynyl]-3-phenyl-3-(4-pyrrolidinophenyl)-3H-naphtho[2,1-b]pyran 3-(2-Fluorophenyl)-6-(5-phenyl-2-thienyl)-3-(4-pyrrolidinophenyl)-3H-naphtho[2,1-b]pyran Examples of most preferred compounds of formula (I)-(II) are the compounds represented by the following formulae Example (a)-Example (f)

Example a

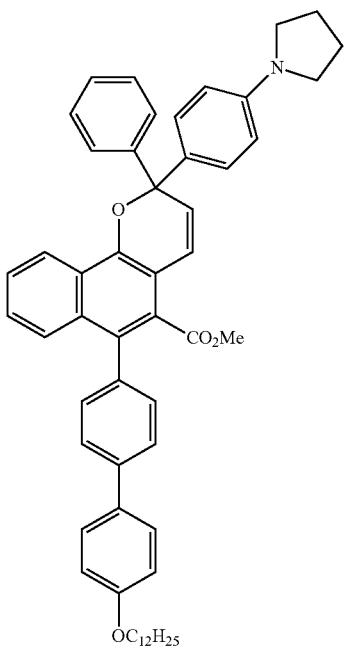

Example b

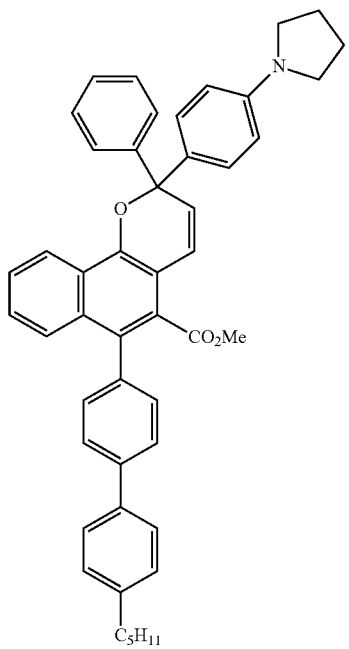

Example c

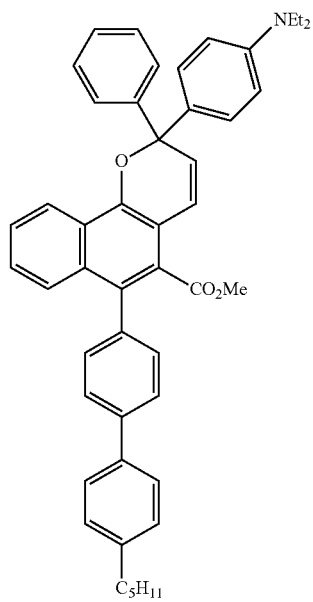

Example d

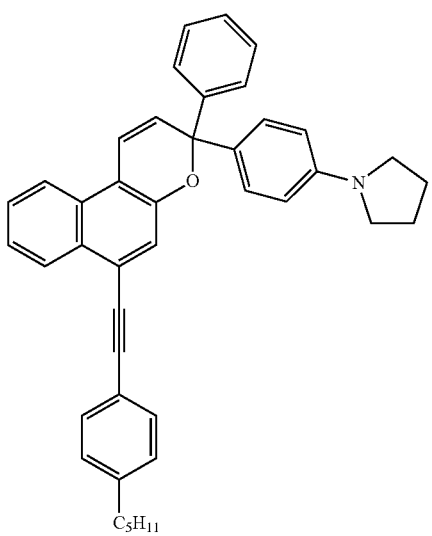

Example e

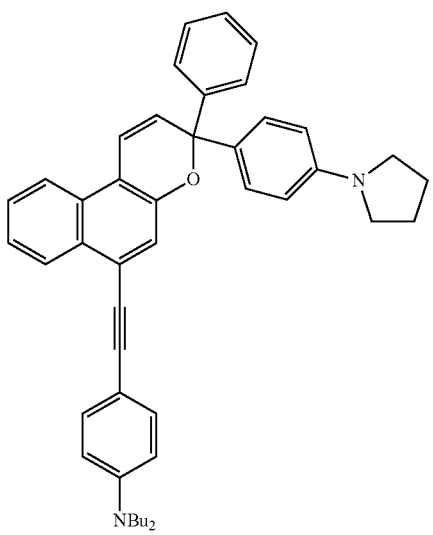

Example f

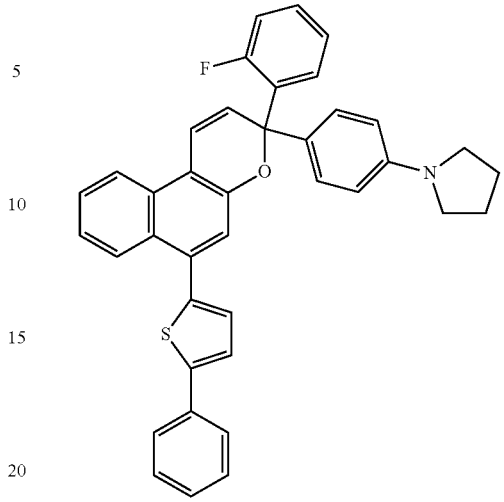

Compounds represented by formula (I) or (II) may be prepared according to the following description and schemes:

The requisite naphthols and naphthopyrans may be prepared as shown in Schemes 1-4. For example, methyl 1,4-dihydroxynaphthalene-2-carboxylate 1 may be obtained by selective methylation of commercially available 1,4-dihydroxy-2-naphthoic acid according to the literature procedure (T. Hattori, N. Harada, S. Oi, H. Abe, and S. Miyano, *Tetrahedron: Aysmmetry,* 1995, 6, 1043). Subsequent acid-catalysed condensation of 1 with 1,1-diarylprop-2-yn-1-ols 2 affords the 6-hydroxynaphtho[1,2-b]pyrans 3. This route to naphthopyrans has been reviewed (B. Van Gemert, *Organic Photochromic and Thermochromic Compounds Volume 1: Main Photochromic Families*, Ed. J. C. Crano and R. Gugglielmetti, Plenum Press, New York, 1998, p. 111; J. D. Hepworth and B. M. Heron, *Functional Dyes*, Ed. S.-H. Kim, Elsevier, Amsterdam, 2006, p. 85) and the synthesis of the requisite alkynols 2 is documented extensively (e.g. C. D. Gabbutt, J. D. Hepworth, B. M. Heron, S. M. Partington and D. A. Thomas, *Dyes Pigm.,* 2001, 49, 65).

Acylation of naphthopyran 3 with trifluoromethanesulfonic anhydride in the presence of base affords the triflates 4 in good yield. These latter compounds may be readily transformed into compounds represented by formula I by Suzuki-Miyaura coupling (A. Suzuki, *J. Organomet. Chem.,* 1999, 576, 147; N. Miyaura, *Top. Curr. Chem.,* 2002, 219, 11) with boronic acids such as 4'-dodecyloxy-4-biphenylboronic acid 5a (A. A. Kiryanov, P. Sampson and A. J. Seed, *J. Mater. Chem.,* 2001, 11, 3068) or 4'-n-pentyl-4-biphenylboronic acid 5b (M. R. Friedman, K. J. Toyne, J. W. Goodby and M. Hird, *Liquid Crystals,* 2001, 28, 901) to give pyrans 6a and 6b respectively. The preparation of Examples a-c by this approach are outlined in Scheme 1.

Scheme 1

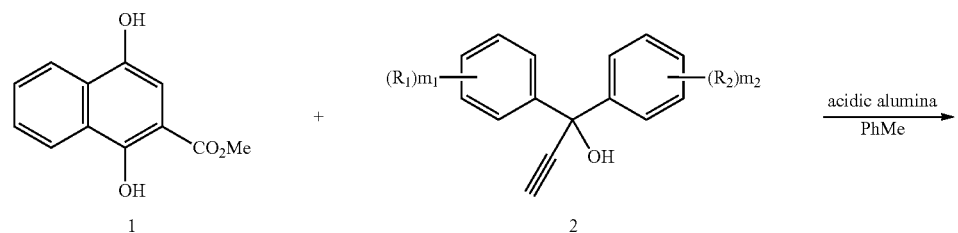

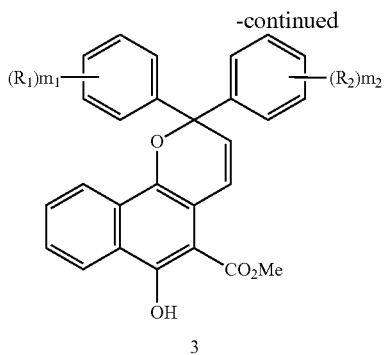
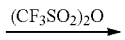

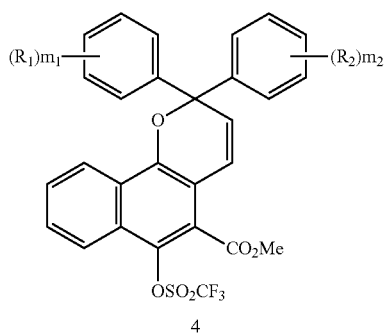
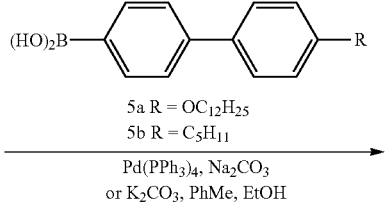

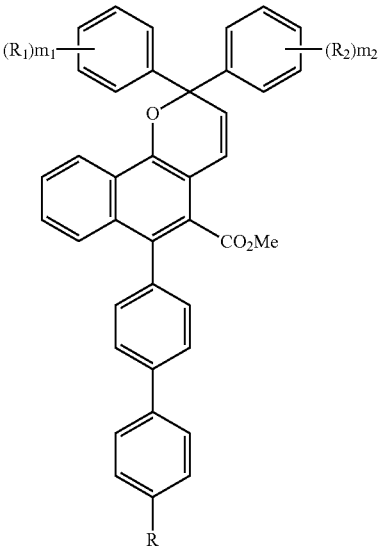

The preparation of the isomeric naphtho[2,1-b]pyrans represented by formula II has been accomplished from 4-(phenylethynyl)-2-naphthols 10a and 10b. Synthesis of the latter commences with Sonogashira coupling of the triisopropylsilyl ether of 4-bromo-2-naphthol (prepared from 1-naphthylamine according to M. S, Newman, V. Sankaran and D. Olson, *J. Am. Chem. Soc.,* 1976, 98, 3237) to phenylacetylenes such as (4-pentylphenyl)acetylene (M. Hird and K. J. Toyne, *Liquid Crystals,* 1993, 14, 741) and (4-dibutylaminophenyl)acetylene (obtained according to the route shown in Scheme 2, J. J. Miller, J. A. Marsden and M. M. Haley, *Synlett,* 2004, 165.) Condensation of 10 with the alkynols 2 gave 11a and 11b as illustrated by Examples d-e. 5-Phenylthiophene-2-boronic acid, prepared from 2-phenylthiophene according to the literature procedure (T. J. Dingemans, N. S, Murthy and E. T. Samulski, *J. Phys. Chem. B,* 2001, 105, 8845) has been coupled to the triflate 12 (S. C. Benson, J. Y. L. Lam, S. M. Menchen, U.S. Pat. No. 5,936,087) to give 2-naphthol 13 following demethylation with $BBr_3$. Subsequent condensation with 2 under acidic conditions provides 14, illustrated by Example f. Routes to all of the starting materials and naphthopyrans are shown in Scheme 3.

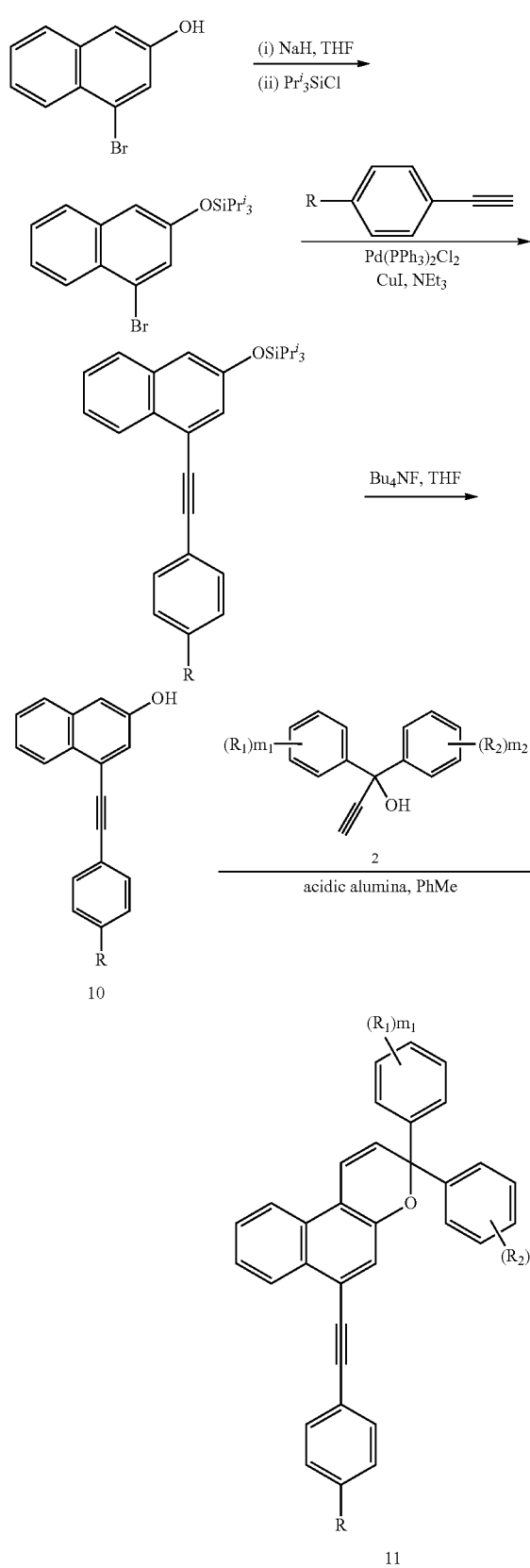
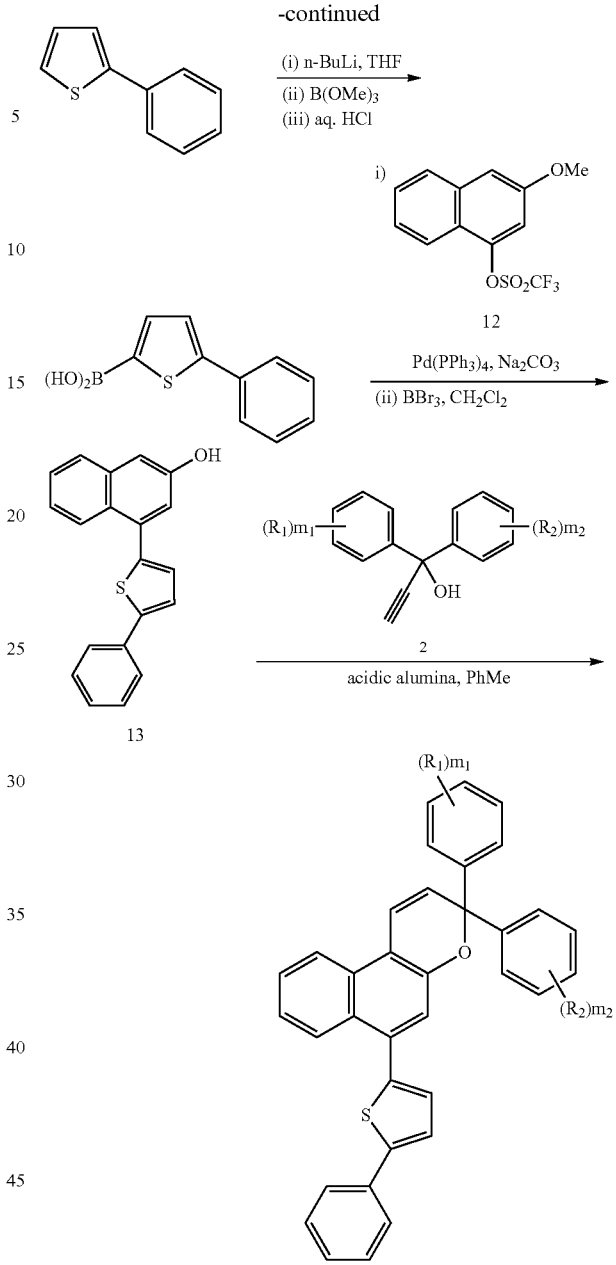

The photochromic compounds of the invention may be used alone, in combination with other naphthopyran of the invention, and/or in combination with one or more other appropriate complementary organic photochromic materials, i.e. an organic compound having at least one activated absorption maxima within the range of between about 400 to 700 nanometers. Compatible dyes or pigments may be also mixed with the photochromic dyes of the present invention, to achieve for example a more aesthetic result, a more neutral colour or absorb a particular wavelength of incident light, or to provide a desired hue.

The present invention also provides an optical article comprising one or more naphthopyran compounds of formulae (I)-(II) of the present invention. The naphthopyran compounds of formulae (I)-(II) of the present invention can be used in all kinds of optical devices and elements, such as ophthalmic elements and devices, display elements and devices, windows or mirrors. Non-limiting examples of ophthalmic elements include corrective and non-corrective lenses, including single vision or multi-vision lenses, which may be either segmented or non-segmented, as well as other elements used to correct, protect, or enhance vision, including without limitation contact lenses, intra-ocular lenses, magnifying lenses and protective lenses or visors. Non-limiting examples of display elements and devices include screens and monitors. Non-limiting examples of windows include automotive and aircraft transparencies, filters, shutters, and optical switches.

The optical article of the present invention is preferably a lens, and more preferably an ophthalmic lens.

When used in optical articles, the naphthopyran compounds can be incorporated, for example, in the bulk of a polymeric material of the optical article. Such a polymeric host material is generally a solid transparent or optically clear material. Preferred polymeric host materials are for example polymers of polyol(allyl carbonate) monomers, polyacrylates, poly(triethyleneglycol dimethacrylate), polyperfluoroacrylates, cellulose acetate, cellulose triacetate, cellulose acetate propionate, cellulose acetate butyrate, poly(vinyl acetate), poly(vinyl alcohol), polyurethanes, polycarbonates, poly(ethylene terephthalate), polystyrene, polyfluorostyrene, poly(diethylene glycol bis(alkyl carbonate)) and mixtures thereof.

The photochromic substances of the present invention may be incorporated into the polymeric host material by various methods described in the art. Such methods include dissolving or dispersing the photochromic substance within the host material by adding it to the monomeric host material prior to polymerization, or by imbibition of the photochromic substance into the host material by immersion of the host material in a hot solution of the photochromic substance.

In another preferred embodiment of the present invention the photochromic dyes are not incorporated into the bulk of an organic polymeric host material, but are incorporated into a surface coating or a film applied onto an optical substrate. The substrate is preferably a transparent or optically clear material, such as glass or organic polymers commonly used in optical applications.

The present invention of course also encompasses optical articles having at least one naphthopyran compound of formula (I)-(II) incorporated either in the bulk of the article, or in the coating of the article, or in the film applied onto the article.

In a still more preferred embodiment of the present invention, the coating or film incorporating the photochromic naphthopyran compounds of the present invention is an anisotropic film or coating, i.e. it comprises a layer or medium which is able to function as an alignment layer for the dye molecules. Such an alignment layer may be for example an organic polymer, such as polyvinyl alcohol (PVA). One common method of aligning the molecules of a dichroic dye involves heating a sheet or layer of PVA to soften the PVA and then stretching the sheet to orient the polymer chains. The dichroic dye is then impregnated into the stretched sheet and dye molecules take the orientation of the polymer chains. Alternatively, the dichroic dye can be first impregnated into the PVA sheet, and thereafter the sheet can be heated and stretched as described above to orient the PVA polymer chains and associated dyes. In this manner, the molecules of the dichroic dye can be suitably positioned or arranged within the oriented polymer chains of the PVA sheet and a net linear polarization can be achieved.

In an even more preferred embodiment of the present invention, the novel naphthopyran compounds are not incorporated into a solid, isotropic or anisotropic host material, but into a fluid, mesomorphous or gel host medium. Dissolving or dispersing the naphthopyran compounds of the present invention in such a fluid, mesomorphous or gel host medium increases the coloration rate and even more drastically the fading rate. The recovery time, i.e. the time it takes the material to revert from an absorptive condition to a clear condition, can thus be reduced to less than 5 minutes.

The fluid or mesomorphous host medium incorporating at least one naphthopyran compound is preferably selected from the group consisting of organic solvents, ionic solvents, liquid crystals, and mixtures thereof.

The naphthopyran compounds of the present invention are preferably dissolved in the host medium.

The organic solvents may be selected for example from the group comprising of benzene, toluene, methyl ethyl ketone, acetone, ethanol, tetrahydrofurfuryl alcohol, N-methylpyrrolidone, 2-methoxyethyl ether, xylene, cyclohexane, 3-methylcyclohexanone, ethyl acetate, ethyl phenylacetate, ethyl methoxyphenyl acetate, propylene carbonate, diphenylmethane, diphenylpropane, tetrahydrofuran, methanol, methyl propionate, ethylene glycol and mixtures thereof.

The liquid crystal medium that may be used in the present invention includes, without being limited to, such materials as nematic or chiral nematic media. Alternatively a polymeric liquid crystal medium can be used as the host material. These liquid crystal and polymeric liquid crystal media are generally used in combination with an organic solvent, for example one of the organic solvents mentioned above.

The mixture of a fluid, mesomorphous or gel host medium and at least one of the naphthopyran compounds of the present invention preferably is incorporated into a device containing a mechanism for holding the mixture in a mechanically stable environment.

A preferred device for holding the mixture in a mechanically stable environment is the one described in WO 2006/013250 and FR 2879757, which are hereby specifically incorporated by reference herein.

The preferred optical article of the present invention, disclosed in WO 2006/013250, comprises an optical component provided with at least one transparent cell arrangement juxtaposed in a parallel direction to the surface thereof, each cell being tightly closed and containing said fluid, mesomorphous or gel host medium and said at least one naphthopyran compound of the present invention. The transparent cell arrangement forms a layer whose height perpendicular to the component surface is less than 100 μm, preferably comprised between 1 μm and 50 μm.

The transparent cell arrangement may be formed either directly on a transparent rigid substrate of said optical component, or alternatively a transparent film incorporating the transparent cell arrangement may be applied on a transparent rigid substrate of the optical component.

The cell arrangement preferably occupies a large fraction of the total surface of the optical component. The ratio of the total surface occupied by the cells to the total surface of the optical component is preferably at least 90%, more preferable comprised between 90 and 99.5%, and most preferably between 96% and 98.5%.

The cell arrangement may be composed for example of hexagonal or rectangular cells, whose dimensions may be described by
  (a) their size parallel to the surface of the optical component, which is preferably of at least 1 μm, more preferably comprised between 5 μm and 100 μm;
  (b) the height of the cells perpendicular to the component surface, which is preferably less than 100 μm, and is more preferably comprised between 1 μm and 50 μm; and
  (c) the thickness of the partitions separating the tightly closed cells from each other, which is preferable comprised between 0.10 and 5.00 μm.

EXAMPLES

Synthesis of Intermediate Compounds used in the Synthesis of Example Compounds

Methyl 1,4-dihydroxynapthalene-2-carboxylate

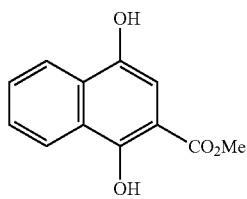 [SMILES: COC(=O)c1cc(O)c2ccccc2c1O]

1,4-Dihydroxy-2-naphthoic acid (10 g, 49 mmol) and NaHCO$_3$ (4.12 g, 49 mmol) was dissolved in DMF (dimethylformamide) (50 mL). Methyl iodide (6.96 g, 49 mmol) was added and the solution stirred at room temperature for 24 h, poured into water (1 L), filtered and washed with water to give the title compound (8.80 g, 82%) as a green powder.

4-Bromo-2-triisopropylsiloxynaphthalene

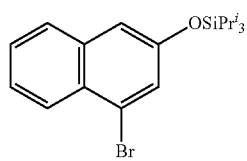

Sodium hydride (0.38 g, 15.9 mmol) was added portionwise to a solution of 4-bromo-2-naphthol (3.54 g, 15.9 mmol) in THF (50 mL) with stirring at 0° C. under N$_2$. Ater 0.5 h chlorotriisopropylsilane (3.06 g, 15.9 mmol) was added dropwise at 0. The solution was stirred at room temperature for 2 h, poured into water (200 mL), extracted with DCM (dichloromethane) (4×50 mL), dried (MgSO$_4$) and the solvent removed under reduced pressure. The residue was chromatographed on silica using hexanes as eluent. The solvent was removed under reduced pressure to give the title compound (5.78 g, 96%) as a colourless oil.

1-(4-Pentylphenyl)ethynyl-3-triisopropylsiloxynaphthalene

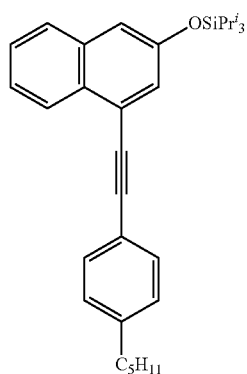

A solution of 3-triisopropylsilyoxy-1-bromonaphthalene (2.32 g, 6.1 mmol), (4-pentylphenyl)acetylene (1.58 g, 9.2 mmol), Pd(PPh$_3$)$_2$Cl$_2$ (129 mg, 3 mol %), PPh$_3$ (240 mg, 15 mol %) and CuI (88 mg, 7.5 mol %) in Et$_3$N (20 mL) under N$_2$ was heated at reflux for 4 h. The resulting mixture was cooled, diluted with Et$_2$O, filtered and the solvent removed under reduced pressure. The residue was chromatographed on silica using hexanes as eluent. The solvent was removed under reduced pressure to give the title compound (0.95 g, 33%) as a pale yellow oil.

4-Iodo-N,N-dibutylaniline

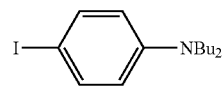

Iodine (7.88 g, 31 mmol) was added portionwise to a mixture of N,N-dibutylaniline (7 g, 34 mmol) and NaHCO$_3$ (2.87 g, 34 mmol) in water (25 mL) with stirring at 10-15° C. After 1 h the mixture was poured into Et$_2$O (200 mL), washed with water (100 mL), Na$_2$S$_2$O$_3$ (2×100 mL), water (2×100 mL), dried (MgSO$_4$) and the solvent removed under reduced pressure. The residue was chromatographed on silica using hexane as eluent. The first fraction was collected and the solvent removed under reduced pressure to give the title compound (7.26 g, 71%) as a pale brown oil.

4-Trimethysilylethynyl-N,N-dibutylaniline

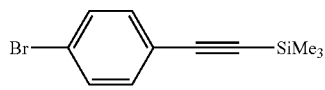

Cuprous iodide (23 mg, 1 mol %) was added to 4-iodo-N,N-dibutylaniline (4 g, 12.1 mmol), trimethylsilylacetylene (2.37 g, 24.2 mmol) and Pd(PPh$_3$)$_2$Cl$_2$ (84 mg, 1 mol %) in dry Et$_3$N (40 mL) under nitrogen. The resulting solution was stirred at room temperature for 16 h, diluted with benzene (50 mL), filtered and the solvent removed under reduced pressure. The residue was chromatographed on alumina using benzene as eluent. The solvent was removed under reduced pressure to give the title compound (3.0 g, 82%) as a pale yellow oil.

4-Ethynyl-N,N-dibutylaniline

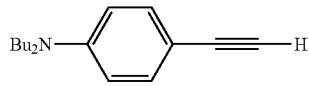

Potassium hydroxide (5 mL, 2 M) was added to a solution of 4-trimethysilylethynyl-N,N-dibutylaniline (3 g, 9.1 mmol) in MeOH (100 mL) with stirring. The solution was stirred at 40° C. for 0.5 h, poured into water (200 mL), extracted with Et$_2$O (3×50 mL), washed with water (50 mL), dried (MgSO$_4$) and the solvent removed under reduced pressure to give the title compound (2.35 g, 100%) as a brown oil.

3-[(4-Dibutylaminophenyl)ethynyl]-2-naphthol

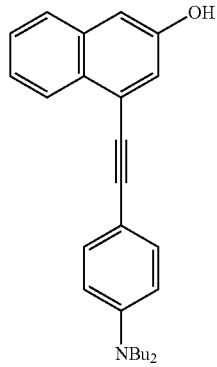

A solution of 3-triisopropylsilyoxy-1-bromonaphthalene (3.17 g, 8.4 mmol), 4-ethynyl-N,N-dibutylaniline (2.87 g, 12.5 mmol), Pd(PPh$_3$)$_2$Cl$_2$ (176 mg, 3 mol %), PPh$_3$ (329 mg, 15 mol %) and CuI (120 mg, 7.5 mol %) in Et$_3$N (20 mL) under N$_2$ was heated at reflux for 3 h. The resulting mixture was cooled, poured into water (200 mL), extracted with DCM (3×50 mL), dried (MgSO$_4$) and the solvent removed under reduced pressure. The residue was chromatographed on silica using DCM (20% in hexanes) as eluent. The solvent was removed under reduced pressure and the residue dissolved in Et$_2$O (30 mL). Tetrabutylammonium fluoride (3.8 mL, 1 M, 3.8 mmol) was added and stirring continued for 10 min. The solution was poured into water (100 mL), extracted with Et$_2$O (3×40 mL), dried (MgSO$_4$) and the solvent removed under reduced pressure. The residue was filtered through a short plug of silica using DCM (15% in hexanes to 0% in EtOAc gradient) as eluent. The solvent was removed under reduced pressure to give the title compound (1.40 g, 21%) as a brown oil.

4-Bromo-4'-(dodecyloxy)biphenyl

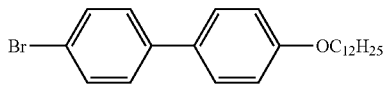

A mixture of 4'-bromobiphenyl-4-ol (8.41 g, 33.8 mmol), 1-iodododecane (10 g, 33.8 mmol) and K$_2$CO$_3$ (18.64 g, 135 mmol) in butanone (100 mL) was heated at reflux. After 16 h the mixture was poured into water (200 mL), extracted with DCM (3×100 mL), washed with NaOH (2 M, 100 mL), dried (MgSO$_4$) and the solvent removed under reduced pressure. The residue was washed with hot MeOH to give the title compound (13.37 g, 95%) as a colourless powder.

4'-Dodecyloxy-4-biphenylboronic acid

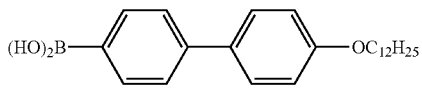

Butyllithium (6 ml, 1.6 M in hexanes, 9.6 mmol) was added dropwise to a solution of 4-bromo-4'-(dodecyloxy)biphenyl (4 g, 9.6 mmol) in THF (tetrahydrofuran) (150 mL) under N$_2$ at −78° C. with stirring. Stirring was continued for 1 h and trimethyl borate (3 g, 28.8 mmol) was added. The resulting mixture was warmed to room temperature overnight, acidified with HCl (2 M, 100 mL), extracted with EtOAc (3×200 ml), dried (MgSO$_4$) and the solvent removed under reduced pressure. The residue was filtered through a short plug of silica using EtOAc (0-100% gradient in DCM) as eluent. The solvent was removed under reduced pressure and the residue washed with hexane to give the title compound (0.84 g, 23%) as a colourless powder.

4'-Pentyl-4-biphenylboronic acid

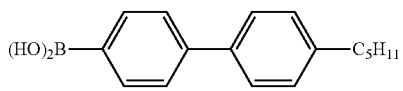

4-Bromo-4'-pentylbiphenyl (3 g, 9.9 mmol) was added in one portion to Mg (0.27 g, 11.1 mmol), treated with I$_2$, in THF (40 mL). The mixture was heated at reflux for 3 h, cooled to −78° C. and trimethyl borate (2.06 g, 19.8 mmol) was added dropwise. The mixture was warmed to room temperature over 1 h, acidified with HCl (2 M, 50 mL), extracted with Et$_2$O (3×50 mL). The combined ethereal washes were extracted with NaOH (100 mL, 1 M). The aqueous phase was acidified with concentrated HCl, extracted with Et$_2$O (3×50 mL), dried (MgSO$_4$) and the solvent removed under reduced to give the title compound (2.07 g, 78%) as an off white powder.

5-Phenyl-2-thiopheneboronic acid

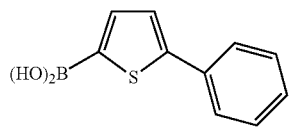 [SMILES: OB(O)c1ccc(-c2ccccc2)s1]

n-Butyllithium (1.6M in hexanes) (24 ml, 38.1 mmol) was added drop wise to a solution of 2-phenylthiophene (6.1 g, 38.1 mmol) in anhydrous THF (150 ml), at 0° C., under nitrogen. The ice-bath was removed, and the mixture heated to reflux for 20 min. After cooling, the reaction mixture was added drop wise to a solution of trimethyl borate (8.7 ml, 76.25 mmol) in anhydrous THF (100 ml), at −78° C., under nitrogen. This was allowed to warm to room temperature overnight, then was acidified with concentrated HCl, stirred for 1 h, then extracted with Et$_2$O (3×100 ml). The combined extracts were washed with water (2×100 ml), dried (Na$_2$SO$_4$), and the solvent removed. The resulting grey solid was recrystallised from ethanol/water (50:50), then dissolved in aqueous NaOH (2M, 500 ml), Et$_2$O (250 ml) added, the aqueous layer precipitated with concentrated HCl, extracted with Et$_2$O (300 ml), dried (Na$_2$SO$_4$) and the solvent removed under pressure to give the title compound (2.72 g, 35%) as an off white solid.

3-Methoxy-1-(5-phenyl-2-thienyl)naphthalene

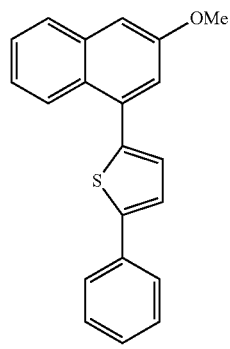 [SMILES: COc1cc(-c2ccc(-c3ccccc3)s2)c2ccccc2c1]

Methyl 6-hydroxy-3-phenyl-3-(4-pyrrolidinophenyl)-2H-naphtho[1,2-b]pyran-5-carboxylate

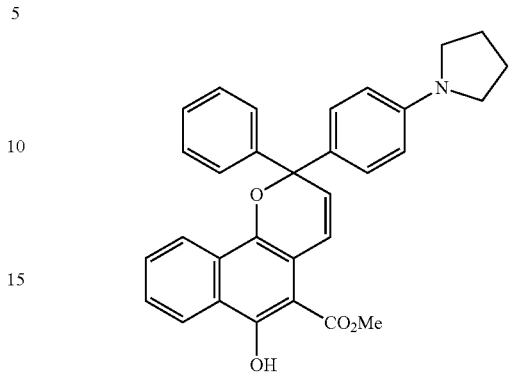

A mixture of 3-methoxynaphthalene-1-yl trifluoromethanesulfonate (2.7 g, 8.82 mmol), 5-phenyl-2-thiopheneboronic acid (2.7 g, 13.24 mmol), sodium carbonate (1.4 g, 13.24 mmol) was mixed in de-gassed toluene (50 ml) and ethanol (50 ml), under nitrogen. Pd(PPh$_3$)$_4$ (153 mg, 1 mol %) was added and the mixture heated to reflux for 18 h. The solution was allowed to cool, poured into water (200 ml), extracted with dichloromethane (2×100 ml), dried (Na$_2$SO$_4$), and the solvent removed under reduced pressure. The resulting residue was dissolved in DCM and filtered through a short plug of silica. The solvent was removed under reduced pressure to give a red/brown solid, which was flash chromatographed on silica using EtOAc-hexane (1:9). The fractions were combined and the solvent removed to give the title compound (1.87 g, 67%) as a green solid.

A mixture of methyl 1,4-dihydroxynaphthalene-2-carboxylate (3.93 g, 18 mmol), 1-phenyl-1-(4-pyrrolidinophenyl)prop-2-yn-1-ol (5 g, 18 mmol) and Al$_2$O$_3$ (4 g) in PhMe (100 mL) was heated at reflux for 1.5 h, cooled, filtered, the residue washed with DCM and the solvent removed under reduced pressure. The residue was filtered through a short plug of silica using DCM (40% in hexanes) as eluent. The solvent was removed under reduced pressure and the residue was crystallized from Et$_2$O-hexanes to give the title compound (5.47 g, 62%) as a yellow powder.

Methyl 2-(4-diethylaminophenyl)-6-hydroxy-2-phenyl-2H-naphtho[1,2-b]pyran-5-carboxylate

4-(5-Phenyl-2-thienyl)-2-naphthol

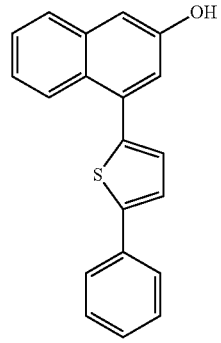 [SMILES: Oc1cc(-c2ccc(-c3ccccc3)s2)c2ccccc2c1]

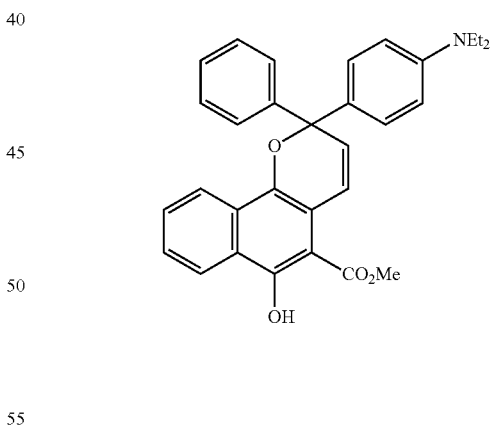

Boron tribromide (1.04 ml, 10.76 mmol) was added slowly to a solution of 3-methoxy-1-(5-phenyl-2-thienyl)naphthalene (1.7 g, 5.38 mmol) in dichloromethane (50 ml) at 0° C. under nitrogen. After the addition was complete, the solution was allowed to stir for 20 h. The mixture was then poured into water (200 ml), extracted with Et$_2$O (2×100 ml), washed with water (100 ml), dried (Na$_2$SO$_4$) and the solvent removed under reduced pressure. The resulting solid was washed with hexane and filtered to afford the title compound (1.47 g, 91%) as a red solid.

Methyl 1,4-dihydroxynaphthalene-2-carboxylate (4.00 g, 18.3 mmol), 1-(4-diethylaminophenyl)-1-phenyl-prop-2-yn-1-ol (4.67 g, 18.3 mmol) and Al$_2$O$_3$ (4.5 g) in toluene (150 mL) was refluxed for 3 hrs, filtered whilst hot and the solvent removed under reduced pressure. The residue was filtered through a short plug of silica using DCM (20% hexane) as eluent followed by a second filtration through silica using DCM as eluent. The residue was crystallised from acetone-MeOH and the product isolated as a yellow solid (4.89 g, 56%)

Methyl 6-Trifluoromethanesulfonyloxy-3-phenyl-3-(4-pyrrolidinophenyl)-2H-naphtho-[1,2-b]pyran-5-carboxylate

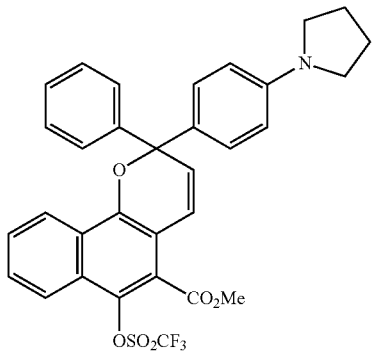

Trifluoromethanesulfonic anhydride (5.32 g, 18.9 mmol) was added dropwise to a solution of 6-hydroxy-5-methoxycarbonyl-3-phenyl-3-(4-pyrrolidinophenyl)-2H-naphtho-[1,2-b]pyran (4.8 g, 10 mmol) and pyridine (1.7 g, 21.6 mmol) in DCM (100 mL) at 0° C. under $N_2$ with stirring. After 1 h the resulting solution was washed with HCl (100 mL, 2 M), water (100 mL), dried (MgSO$_4$) and the solvent removed under reduced pressure. The residue was filtered through a short plug of silica using DCM as eluent. The solvent was removed under reduced pressure to give the title compound (3.57 g, 58%) as a blue powder.

Methyl 2-(4-diethylaminophenyl)-2-phenyl-6-trifluoromethanesulfonyloxy-2H-naphtho[1,2-b]pyran-5-carboxylate

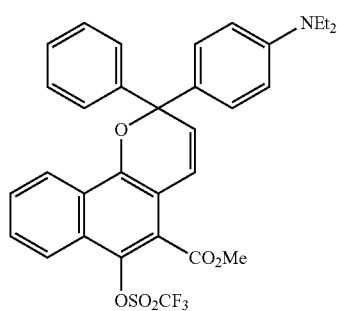

Pyridine (0.17 mL, 2.1 mmol) was added to methyl 2-(4-diethylaminophenyl)-6-hydroxy-2-phenyl-2H-naphtho[1,2-b]pyran-5-carboxylate (1.00 g, 2.1 mmol) in DCM under $N_2$ at 0° C. Trifluoromethanesulfonic anhydride was added dropwise to the mixture and the solution was warmed to room temperature and stirred for 1 h. HCl (100 mL, 2 M) was added, the aqueous phase separated, extracted with DCM (3×50 mL). The combined organic phases were washed with water (100 mL), dried (MgSO$_4$) and the solvent removed under reduced pressure. The residue was filtered through a short plug of silica using DCM as eluent and the solvent was removed to give the product as a blue powder (0.91 g, 72%)

THE FOLLOWING EXAMPLES WERE PREPARED USING THE INTERMEDIATE STEPS DESCRIBED HEREINBEFORE

Example a

Methyl 6-(4'-dodecyloxy-biphenyl-4-yl)-2-phenyl-2-(4-pyrrolidinophenyl)-2H-naphtho[1,2-b]pyran-5-carboxylate

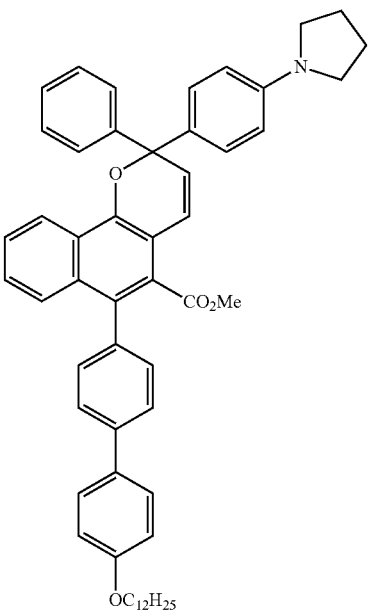

A mixture of methyl 6-trifluoromethanesulfonyloxy-3-phenyl-3-(4-pyrrolidinophenyl)-2H-naphtho[1,2-b]pyran-5-carboxylate (0.96 g, 1.6 mmol), 4'-dodecyloxy-4-biphenylboronic acid (0.6 g, 1.6 mmol), Na$_2$CO$_3$ (0.42 g, 3.2 mmol) and Pd(PPh$_3$)$_4$ in PhMe (30 mL) and EtOH (30 mL) was heated at reflux for 4 h. The resulting solution was cooled, poured into water (100 mL), extracted with DCM (4×50 mL), dried (MgSO$_4$) and the solvent removed under reduced pressure. The residue was chromatographed on silica using EtOAc (10% in hexanes), then again using PhMe (80% in hexanes). The solvent was removed under reduced pressure and the residue crystallized from DCM/ligroin to give the title compound (0.20 g, 16%) as a blue powder.

Example B

Methyl 6-(4'-pentylbiphenyl-4-yl)-2-phenyl-2-(4-pyrrolidinophenyl)-2H-naphtho[1,2-b]pyran-5-carboxylate

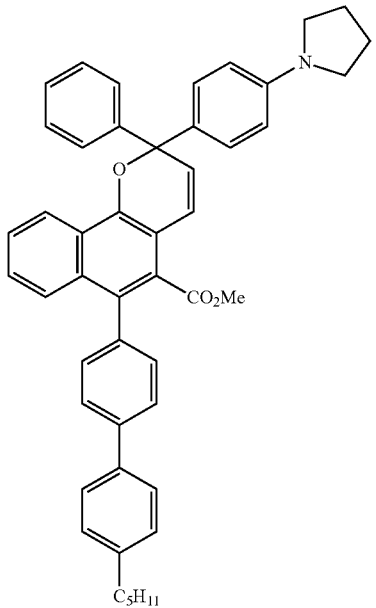

A mixture of 6-trifluoromethanesulfonyloxy-5-methoxycarbonyl-3-phenyl-3-(4-pyrrolidinophenyl)-2H-naphtho[1,2-b]pyran (0.96 g, 1.6 mmol), 4'-pentyl-4-biphenylboronic acid (0.66 g, 2.5 mmol), $K_2CO_3$ (0.68 g, 49 mmol) and $Pd(PPh_3)_4$ (91 mg, 3 mol %) in PhMe (30 mL) and EtOH (30 mL) was heated at reflux for 2 h. The resulting solution was cooled, poured into water (100 mL), extracted with DCM (4×50 mL), dried ($MgSO_4$) and the solvent removed under reduced pressure. The residue was chromatographed twice on silica using PhMe (80% in hexanes). The solvent was removed under reduced pressure and the residue crystallized from acetone-MeOH to give the title compound (0.36 g, 32%) as a purple powder.

Example c

Methyl 2-(4-diethylaminophenyl)-2-phenyl-6-(4'-pentylbiphenyl-4-yl)-2H-naphtho[1,2-b]pyran-5-carboxylate

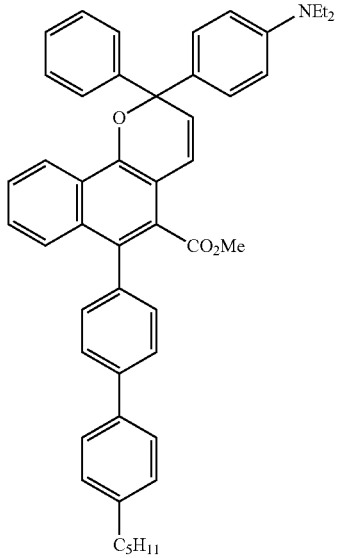

A solution containing methyl 2-(4-diethylamino-phenyl)-2-phenyl-6-trifluoromethanesulfonyloxy-2H-naphtho[1,2-b]pyran-5-carboxylate (0.90 g, 1.47 mmol), 4'-pentyl-4-biphenylboronic acid (0.39 g. 1.47 mmol), $K_2CO_3$ (0.30 g), PhMe (30 mL), ethanol (30 mL) and degassed for 1 h. $Pd(PPh_3)_4$ (0.085 g, 5% mol) was added and the reaction mixture was heated at reflux for 16 hrs. The reaction mixture was poured into water (100 mL), extracted with DCM (4×50 mL), dried (MgSO4) and the solvent removed under reduced pressure. The residue was chromatographed on silica using DCM (20% hexanes) and recrystallised from acetone-MeOH to give a pale blue powder (2.3 g, 30%) mp: 177-178° C.

Example e

6-[(4-Dibutylaminophenyl)ethynyl]-3-phenyl-3-(4-pyrrolidinophenyl)-3H-naphtho[2,1-b]pyran

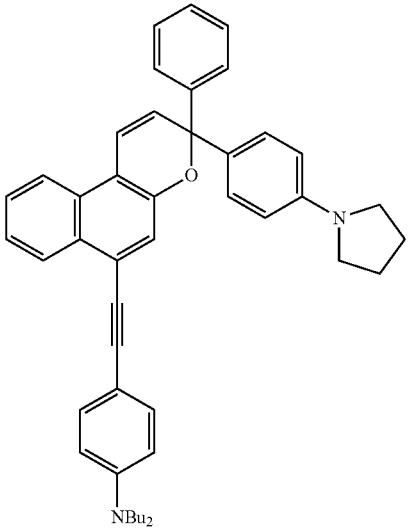

A mixture of 3-[(4-dibutylaminophenyl)ethynyl]-2-naphthol (1.17 g, 3.2 mmol), 1-phenyl-1-pyrrolidinophenyl-prop-2-yn-1-ol (0.87 g, 3.2 mmol) and $Al_2O_3$ (1 g) in PhMe (50 mL) was heated at reflux for 2 h. The solution was filtered hot and the residue washed with hot PhMe (100 mL). The solvent was removed under reduced pressure and the residue chromatographed on neutral alumina using EtOAc (10% in hexanes) then again using EtOAc (5% in hexanes). The solvent was removed under reduced pressure and the residue crystallised from acetone-MeOH to give the title compound (1.27 g, 64%) as a green powder.

Compound of example d could be obtained using 3-[(4-pentylphenyl)ethynyl]-2-naphthol.

Example f 3-(2-Fluorophenyl)-6-(5-phenyl-2-thienyl)-3-(4-pyrrolidinophenyl)-3H-naphtho[2,1-b]pyran

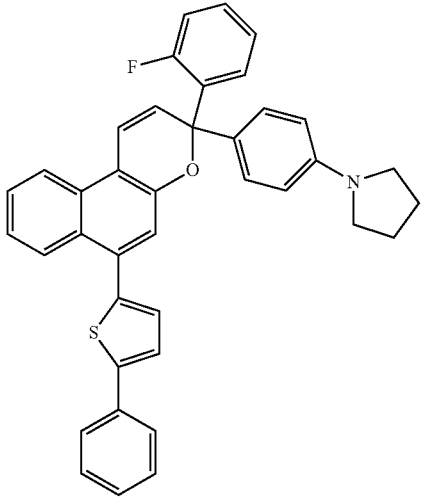 [SMILES: Fc1ccccc1C1(c2ccc(N3CCCC3)cc2)C=Cc2c(cc(-c3ccc(-c4ccccc4)s3)c3ccccc23)O1]

A stirred solution of 4-(5-phenyl-2-thienyl)-2-naphthol, (0.52 g, 1.73 mmol) and 1-(2-fluorophenyl)-1-(4-pyrrolidinophenyl)prop-2-yn-1-ol (0.51 g, 1.73 mmol) in toluene (50 ml) was warmed to 50° C. Acidic $Al_2O_3$ (1 g) was then added and the mixture heated to reflux for 1.5 h. After cooling, the solution was filtered, washed with hot toluene (100 ml) and the solvent removed. The resulting residue was then flash chromatographed eluting with EtOAc-hexane (1:9). The fractions were combined and the solvent removed. After precipitation from acetone-MeOH, the title compound (0.52 g, 52%) was collected as dark green crystals.

The invention claimed is:

1. A naphthopyran compound represented by the formulae (I) to (II)

Formula I

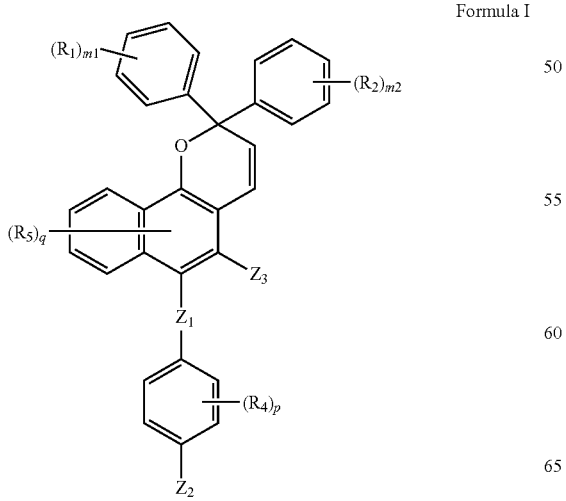

Formula II

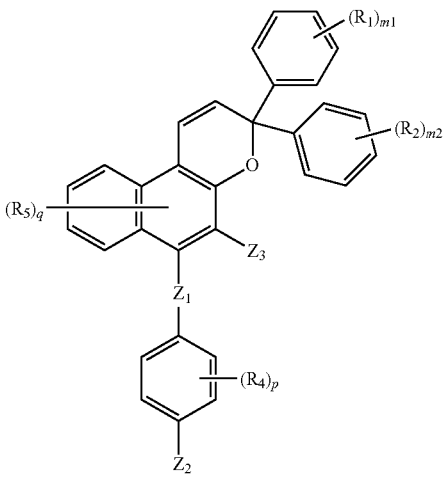

wherein:
$m_1$ is an integer comprised from 0 to 5 inclusive;
$m_2$ is an integer comprised from 0 to 5 inclusive;
p is an integer comprised from 0 to 4 inclusive;
q is equal to 0
$R_1$, $R_2$ and $R_4$, identical or different, independently from each other, represent a group selected from halogen, H, —$R_a$, aryl, —OH, —$OR_a$, —SH, —$SR_a$, —$NH_2$, —$NR_aR_{a1}$, —$NR_bR_c$, —$NR_{a1}COR_a$, —$NR_{a1}CO$(aryl), —$NR_{a1}$aryl, —N-aryl$_2$, —N(aryl)CO(aryl), —$CO_2R_a$, —$CO_2R_{a1}$, —OC(O)—$R_d$, and —X—($R_e$)—Y, and linear or branched ($C_1$-$C_{18}$) perfluoroalkyl group, wherein:
$R_a$ represents a linear or branched ($C_1$-$C_{18}$) alkyl group or linear or branched ($C_1$-$C_{18}$) perfluoroalkyl group;
$R_{a1}$ represents a group selected from hydrogen, linear or branched ($C_1$-$C_{18}$) alkyl group, and linear or branched ($C_1$-$C_{18}$) perfluoroalkyl group;
$R_b$ and $R_c$,
  together and in combination with the nitrogen atom, represent a saturated 5 to 7 membered heterocyclic group which comprises optionally one additional heteroatom selected from O, N and S, and which may be optionally substituted by one or two group(s), identical or different, selected from halogen, —$R_a$, —OH, —$OR_a$, —$NH_2$, and —$NR_aR_{a1}$, wherein $R_a$ and $R_{a1}$ are as defined hereinbefore,
  or together and in combination with the nitrogen atom and the adjacent phenyl group form a heterocyclic group of formula (A), (B), (C) or (D) wherein t is an integer comprised from 0 to 2 inclusive, and $R_a$ and $R_{a1}$ are as defined hereinbefore:

(A)

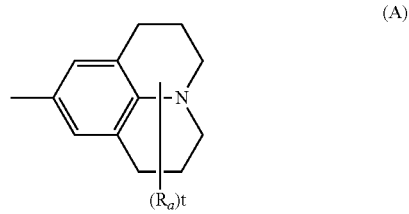

-continued

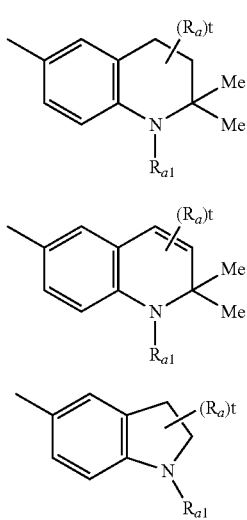

X represents a group selected from oxygen atom, —N($R_{a1}$)—, sulphur atom, —S(O)— and —S($O_2$)— wherein $R_{a1}$ is as defined hereinbefore;

Y represents a group selected from —O$R_{a1}$, —N$R_{a1}R_{a2}$, and —S$R_{a1}$ wherein $R_{a1}$ is as defined hereinbefore and $R_{a2}$ represent a group selected from hydrogen and linear or branched ($C_1$-$C_{18}$) alkyl group;

$R_e$ represents a linear or branched ($C_1$-$C_{18}$) alkylene group, which may be optionally substituted by a group selected from halogen, hydroxyl, linear or branched ($C_1$-$C_6$) alkoxy, and amino;

$R_d$ represents a group selected from linear or branched ($C_1$-$C_{18}$) alkyl group, linear or branched ($C_1$-$C_{18}$) perfluoroalkyl group, —($R_e$)—Y, and aryl group which is optionally substituted by 1 to 4 groups selected from halogen, —$R_a$, —OH, —O$R_a$, —SH, —S$R_a$, —$NH_2$, —N$R_aR_{a1}$, —N$R_bR_c$, —CO—$R_a$, —$CO_2R_{a1}$ wherein $R_a$, $R_{a1}$, $R_b$, $R_c$, $R_d$, $R_e$ and Y are as defined hereinbefore;

$Z_1$ represent a group selected from:

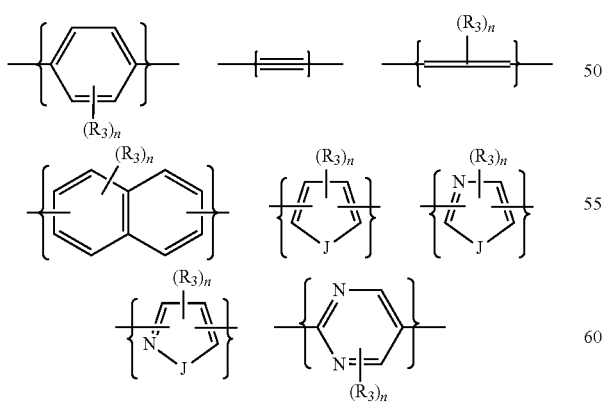

wherein:
$R_3$ represents a group selected from halogen, —$R_a$, —OH, —O$R_a$, —SH, —S$R_a$, —$NH_2$, and —N$R_aR_{a1}$, each or $R_3$ being identical or different;

J is selected from O, S, N$Ra_1$, wherein $R_{a1}$ is as defined hereinbefore;

n is an integer comprised from 0 to 6 inclusive;

$Z_2$ represents a group selected from H, halogen, —$R_a$, —OH, —O$R_a$, —SH, —S$R_a$, —$NH_2$, —N$R_aR_{a1}$, —CO—$R_a$, —$CO_2R_{a1}$, and —O—Z—$R_6$,
wherein $R_a$ and $R_{a1}$ are as defined hereinbefore;

$R_6$ represents a group selected from:
—$R_a$ which may be optionally substituted by a group selected from halogen, —OH, —O$R_a$, —SH, —S$R_a$, —$NH_2$, —N$R_aR_{a1}$, —CO—$R_a$, and —$CO_2R_{a1}$, wherein $R_a$ and $R_{a1}$ are as defined hereinbefore;

cycloalkyl, heterocycloalkyl, aryl, heteroaryl, which may be optionally substituted by 1 to 4 groups selected from halogen, —OH, —O$R_a$, —SH, —S$R_a$, —$NH_2$, —N$R_aR_{a1}$, —CO—$R_a$, —O—C(O)—$R_a$ and —$CO_2R_{a1}$, Z represents a group selected from CO, CS, SO, $SO_2$, $CO_2$, C(O)S, $CS_2$, C(O)NH, C(O)N$R_a$, C(S)NH, C(S)N$R_a$ and C=N$R_a$, wherein $R_a$ is as defined hereinbefore $Z_3$ represents a group selected from hydrogen, —$CO_2R_{a1}$, CHO, —$CH_2$OH, —$CH_2OR_{a1}$, —C$R_aR_{a1}$OH, —$R_{a1}$, and linear or branched ($C_2$-$C_{18}$) alkenyl;

with the provision that for compounds of formula (II) when $Z_1$ represents a group

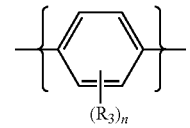

then $Z_3$ is not a hydrogen.

2. The naphthopyran compound according to claim 1, wherein $Z_1$ represent a group selected from:

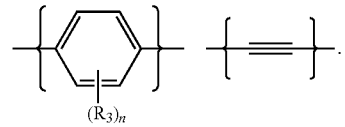

3. The naphthopyran compound of claim 1, selected from one of the following compounds:
Methyl 6-(4'-dodecyloxybiphenyl-4-yl)-2-phenyl-2-(4-pyrrolidinophenyl)-2H-naphtho[1,2-b]pyran-5-carboxylate;
Methyl 2-(4-diethylaminophenyl)-2-phenyl-6-(4'-pentylbiphenyl-4-yl)-2H-naphtho[1,2-b]pyran-5-carboxylate;
Methyl 6-(4'-pentylbiphenyl-4-yl)-2-phenyl-2-(4-pyrrolidinophenyl)-2H-naphtho[1,2-b]pyran-5-carboxylate;
6-[(4-Dibutylaminophenyl)ethynyl]-3-phenyl-3-(4-pyrrolidinophenyl)-3H-naphtho[2,1-b]pyran;
3-(2-Fluorophenyl)-6-(5-phenyl-2-thienyl)-3-(4-pyrrolidinophenyl)-3H-naphtho[2,1-b]pyran.

* * * * *